United States Patent
Zhang

(10) Patent No.: US 10,301,325 B2
(45) Date of Patent: May 28, 2019

(54) QUINOLINE DERIVATIVE, AND PHARMACEUTICAL COMPOSITION, PREPARATION METHOD AND USE THEREOF

(71) Applicant: SHANGHAI HAIJU BIOLOGICAL TECHNOLOGY CO., LTD., Shanghai (CN)

(72) Inventor: Ruling Zhang, Shanghai (CN)

(73) Assignee: SHANGHAI HAIJU BIOLOGICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 15/761,861

(22) PCT Filed: Oct. 29, 2015

(86) PCT No.: PCT/CN2015/093177
§ 371 (c)(1),
(2) Date: May 15, 2018

(87) PCT Pub. No.: WO2017/049711
PCT Pub. Date: Mar. 30, 2017

(65) Prior Publication Data
US 2018/0244695 A1  Aug. 30, 2018

(30) Foreign Application Priority Data
Sep. 24, 2015  (CN) .......................... 2015 1 0617469

(51) Int. Cl.
*A61P 35/00* (2006.01)
*C07D 519/00* (2006.01)
*A61K 31/5383* (2006.01)

(52) U.S. Cl.
CPC ........ *C07D 519/00* (2013.01); *A61K 31/5383* (2013.01); *A61P 35/00* (2018.01); *C07B 2200/07* (2013.01); *C07B 2200/09* (2013.01)

(58) Field of Classification Search
CPC .................................................. C07D 519/00
See application file for complete search history.

(56) References Cited

U.S. PATENT DOCUMENTS

2007/0265272 A1   11/2007   Cheng et al.

FOREIGN PATENT DOCUMENTS

| CN | 103958509 A | 7/2014 |
|---|---|---|
| CN | 105272995 A | 1/2016 |
| WO | 2005004607 A1 | 1/2005 |
| WO | 2005004808 A2 | 1/2005 |
| WO | 2005005378 A2 | 1/2005 |
| WO | 2007075567 A1 | 7/2007 |
| WO | 2008008539 A2 | 1/2008 |
| WO | 2008051808 A2 | 5/2008 |
| WO | 2009091374 A2 | 7/2009 |
| WO | 2013038362 A1 | 3/2013 |
| WO | 2014180182 A1 | 11/2014 |

OTHER PUBLICATIONS

Lee et al. "Gene silencing of c-Met leads to brain metastasis inhibitory effects" Clinical & Experimental Metastasis, 2013, vol. 30, No. 7, pp. 845-854.*
Patani et al. "Bioisosterism: A Rational Approach in Drug Design" Chemical Reviews, 1996, vol. 96, pp. 3147-3176.*
To et al., "The roles of hepatocyte growth factor/scatter factor and Met receptor in human cancers (Review)", Oncology Reports, 5: 1013-1024, 1998.
Rosen et al., "Scatter Factor and Angiogenesis", Advance in Cancer Research, 67:257-279, 1995.
Munshi et al., "ARQ 197, a Novel and Selective Inhibitor of the Human c-Met Receptor Tyrosine Kinase with Antitumor Activity", Mol Cancer Ther 2010; 9:1544-1553 (May 18, 2010).
International Search Report PCT/CN2015/093177 dated Jul. 6, 2017.
Written Opinion PCT/CN2015/093177 dated Jul. 6, 2016.
First Office Action dated Jan. 24, 2017 from Chinese application 201510718743.7.
Second Office Action dated Jun. 9, 2017 fromChinese application 201510718743.7.
Priority application CN201510617469.4 filed on Sep. 24, 2016 (withdrawn, not published).

* cited by examiner

*Primary Examiner* — Joseph R Kosack
(74) *Attorney, Agent, or Firm* — SZDC Law P.C.

(57) ABSTRACT

Disclosed are a quinoline derivative, and a pharmaceutical composition, a preparation method and a use thereof. The quinoline derivative of the present invention has a c-Met inhibitory activity and can be used for the treatment, relieving and/or prevention of cancers or similar diseases.

11 Claims, No Drawings

QUINOLINE DERIVATIVE, AND PHARMACEUTICAL COMPOSITION, PREPARATION METHOD AND USE THEREOF

This application is National Stage Application of PCT/CN2015/093177, filed on Oct. 29, 2015, which claims priority to Chinese Patent Application No. CN 201510617469.4, filed Sep. 24, 2015, which is incorporated by reference for all purposes as if fully set forth herein.

FIELD OF INVENTION

The present invention relates to a quinoline derivative and a pharmaceutical composition, a preparation method and a use thereof.

PRIOR ARTS

Cellular signal transduction is a fundamental mechanism. After the extracellular stimulation signal is transmitted to the interior of the cell, it can regulate a variety of physiological responses of cells, such as cell proliferation, differentiation, apoptosis, and motion etc. Many signal transmission processes utilize the reversible process of protein phosphorylation, involving specific protein kinases and phosphorylase. Protein kinases (PKs) can transfer the phosphate group of ATP to specific amino acid residues of functional proteins and play a very important role in signal transduction.

According to the category of amino acids as substrates in the process of phosphorylation, protein kinases can be classified into serine-threonine kinases (STKs) and tyrosine kinases (PTKs). Tyrosine kinases can be simply classified into receptor type and non-receptor type. Receptor-type tyrosine kinases are a class of relatively large transmembrane kinases and have a ligand-bound extracellular domain, a transmembrane domain and a phosphorylated specific tyrosine residue that functions as a kinase, thus affecting the intracellular domain of cell proliferation. Abnormal expression of the kinases have been found in common human cancers (such as breast cancer, gastrointestinal cancer, blood cancer, ovarian cancer, bronchial cancer, or lung cancer). Therefore, such kinases have become important therapeutic targets.

Hepatocyte growth factor receptor (HGFR, also known as "c-Met") is a class of receptor-type tyrosine kinases. It has been reported that c-Met is overexpressed in various tumors such as pancreatic cancer, gastric cancer, colorectal cancer, breast cancer, prostate cancer, lung cancer, renal cancer, brain tumor, ovarian cancer, and esophageal cancer (refer to Christine T. T. et al., *Oncology Reports*, 5: 1013-1024, 1998). Highly expressed c-Met is closely related to a variety of characteristics of malignant tumors (including abnormal proliferation, invasion, or hypractive metastasis function). It has also been reported that c-Met is also expressed in vascular endothelial cells, which can promote proliferation and migration of vascular endothelial cells to regulate tumor angiogenesis process (*Advance in Cancer Research*, 67:257-279, 1995). Therefore, compounds that can inhibit activities of c-Met kinases are expected to be used as antitumor agents, angiogenesis inhibitors or cancer cell metastasis inhibitors. Inhibition of c-Met signaling pathway is an important strategy for tumor therapy.

There are currently many selective c-Met inhibitors at different research stages. Sugen developed a series of small molecule compounds that can selectively inhibit activities of c-Met kinases at nanomolar level (WO2005004607, WO2005004808, WO2005005378). AMG-208 developed by Amgen is in phase I clinical study (WO2008008539, WO2009091374). Phase I clinical study of SGX126 developed by SGX has been terminated due to its renal toxicity (WO2008051808). JNJ-38877605 developed by Johnson & Johnson (WO2007075567) and PF-04217903 developed by Pfizer (US2007265272) has entered phase I clinical study. However, there is currently no selective c-Met protein kinase inhibitor available on market.

WO2008051808 disclosed a variety of structurally modified c-Met kinase inhibitors, but study of the structure-activity relationship was still relatively lacking and activities of the products were in different levels. For example, $IC_{50}$ values of the compounds of Example 28 and Example 29 were all unsatisfactory, both of which exceed 100 nM, even reach a micromolar level.

WO2013038362 disclosed a series of c-Met kinase inhibitors and study of the structure-activity relationship was also not involved. Examples 18, 26, 28, 34 and 45 all carried out substitution of the nitrogen-containing groups at 3-position of the quinoline ring, but the activities were poor.

WO2014180182 disclosed 3-position and 4-position di-substitution on the quinoline ring, but study of the structure-activity relationship was also not involved, and activities of the compounds differed greatly.

Therefore, there is still no conclusive results of structural elements of small-molecule c-Met kinase inhibitors, and biological activities brought by different structures are still unpredictable. However, the research of novel small-molecule c-Met kinase inhibitors will not only contribute to the establishment of the structure-activity relationship, but also provide new medical directions for the inhibition of c-Met kinases.

CONTENT OF THE PRESENT INVENTION

The technical problem to be solved in the present invention is to provide a quinoline derivative with novel structure, a pharmaceutical composition, a preparation method and a use thereof. The quinoline derivatives of the present invention have c-Met inhibitory activity and can be used for the treatment, alleviation and/or prevention of cancers or similar diseases.

The present invention provides a quinoline derivative, a tautomer, a mesomer, a racemate, an enantiomer, a diastereomer, or a pharmaceutically acceptable salt thereof,

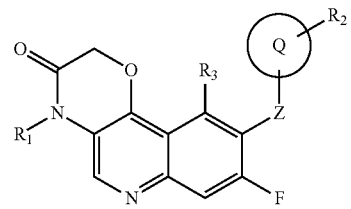

wherein,
$R_1$ is a $C_{1-3}$ alkyl;
$R_2$ is a substituted or unsubstituted 5-6 membered heteroaryl;
$R_3$ is a hydrogen, a $C_{1-3}$ alkyl, a $C_{1-3}$ alkoxy or a halogen;
Z is —$CR^aR^b$ or S; $R^a$ and $R^b$ are each independently a hydrogen, a $C_{1-3}$ alkyl, or a halogen;
Q ring is a substituted or unsubstituted 9-10 membered heteroaryl;

when R₂ is a substituted 5-6 membered heteroaryl, the substituent is selected from the group consisting of $C_{1-3}$ alkyl and $C_{1-3}$ alkoxy;

when Q ring is a substituted 9-10 membered heteroaryl, the substituent is selected from the group consisting of $C_{1-3}$ alkyl and $C_{1-3}$ alkoxy groups;

the heteroatom in the heteroaryl is oxygen, sulfur and/or nitrogen.

In quinoline derivative, the $C_{1-3}$ alkyl in the definition of $R_1$, $R_3$, $R^a$, $R^b$, substituted 5-6 membered heteroaryl and substituted 9-10 membered heteroaryl is independently preferably selected from methyl, ethyl, or isopropyl.

In quinoline derivative, the $C_{1-3}$ alkoxy in substituted 5-6 membered heteroaryl, $R_3$ and substituted 9-10 membered heteroaryl is independently preferably selected from methoxy, ethoxy, or isopropoxy.

In quinoline derivative, the halogen in $R_3$, $R^a$ and $R^b$ is independently preferably selected from fluorine, chlorine, bromine or iodine, more preferred is fluorine.

In quinoline derivative, the 5-6 membered heteroaryl is preferably a 5-6 membered nitrogen-containing heteroaryl, more preferably pyrazolyl or imidazolyl, most preferably

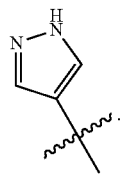

In quinoline derivative, the carbon atom in the definition of 5-6 membered heteroaryl preferably links to Q ring.

In quinoline derivative, when the 5-6 membered heteroaryl is substituted, the substituted position is preferably at heteroatom.

In quinoline derivative, the substituted 9-10 membered heteroaryl is preferably a 9-10 membered nitrogen-containing heteroaryl, preferably a 9-10 membered heteroaryl containing 4 nitrogen atoms, more preferably pyridazinopyrazolyl, more preferably

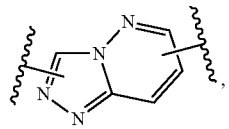

most preferably

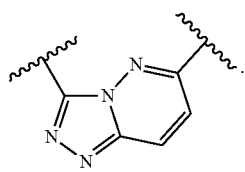 [SMILES: *c1ccc2nnc(*)n2n1]

In quinoline derivative, the 9-10 membered heteroaryl can be a fused ring or a ring system having two rings sharing one bond. When the 9-10 membered heteroaryl contains multiple rings, the ring containing more heteroatoms preferably links to Z.

In quinoline derivative, the carbon atom in 9-10 membered heteroaryl preferably links to Z.

When the 9-10 membered heteroaryl is

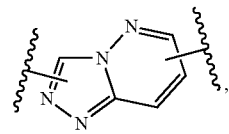

preferably, the triazole moiety links to Z.

In quinoline derivative, when the 9-10 membered heteroaryl is substituted, the substituted position is preferably at the carbon atom.

The quinoline derivative is preferably any of the following compounds;

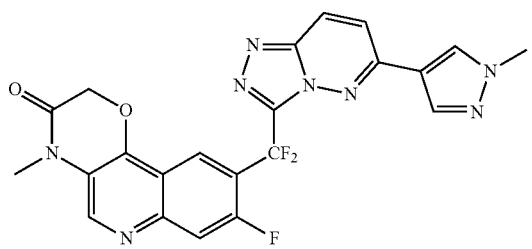 [SMILES: CN1C(=O)COc2c1cnc1cc(F)c(C(F)(F)c3nnc4ccc(-c5cnn(C)c5)nn34)cc21]

9-{difluoro(6-(1-methyl-1H-pyrazol-4-yl)-[1,2,4]triazolo[4,3-b]pyridazin-3-yl)methyl}-8-fluoro-4-methyl-2H-[1,4]oxazino[3,2-c]quinolin-3(4H)-one;

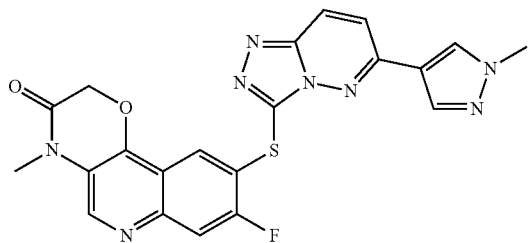 [SMILES: CN1C(=O)COc2c1cnc1cc(F)c(Sc3nnc4ccc(-c5cnn(C)c5)nn34)cc21]

8-fluoro-4-methyl-9-{[6-(1-methyl-1H-pyrazol-4-yl)-[1,2,4]triazolo[4,3-b]pyridazin-3-yl)thio}-2H-[1,4]oxazino[3,2-c]quinolin-3(4H)-one.

The present invention also provides a preparation method of the quinoline derivative, which is selected from:

method 1, when Z is —CR$^a$R$^b$, the method comprises:

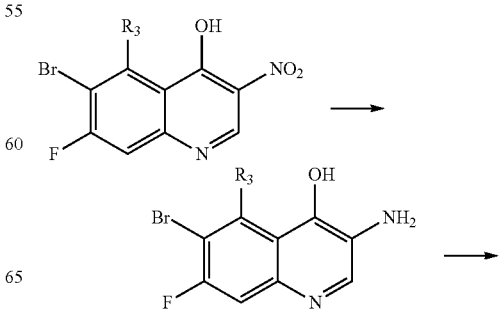

-continued

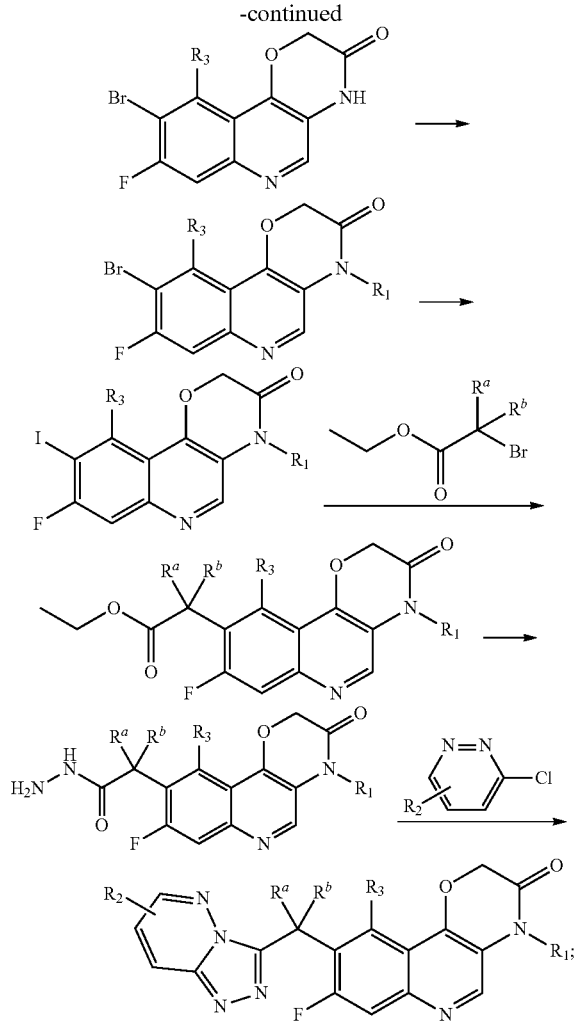

method 2, when Z is S, the method comprises:

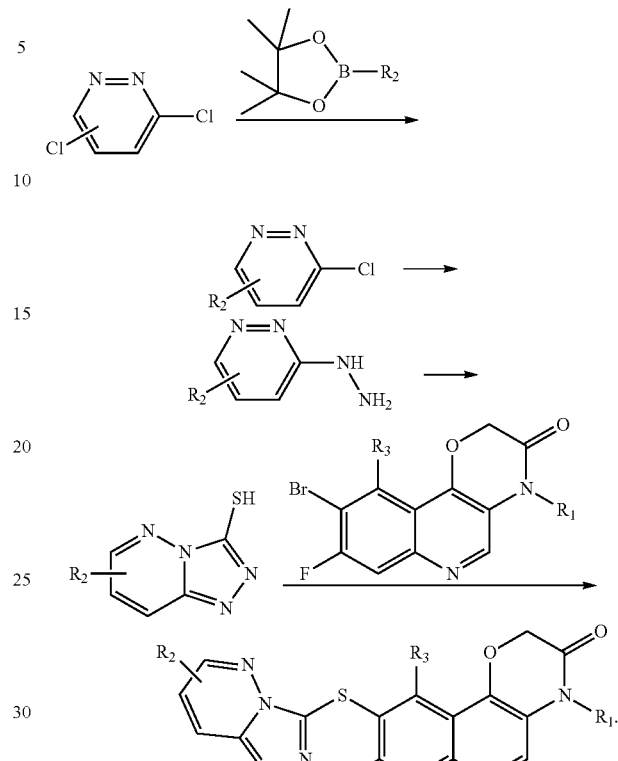

The conditions of each reaction step in the preparation method for the quinoline derivative can be conventional conditions of such reactions in the art. Reference can be made to the method in WO2013038362, the content of which is incorporated herein by reference in its entirety.

In the present invention, method 1 preferably comprises:

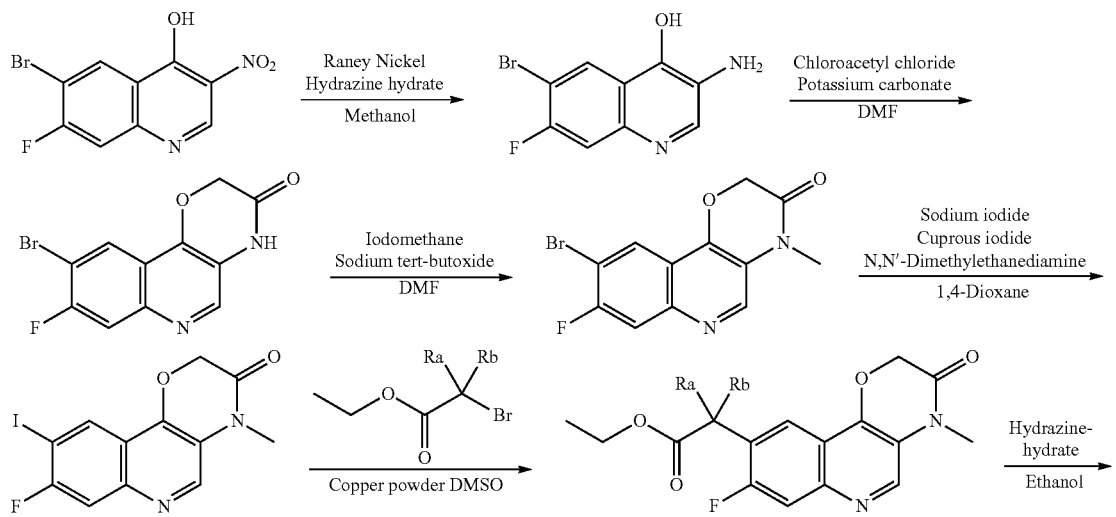

-continued

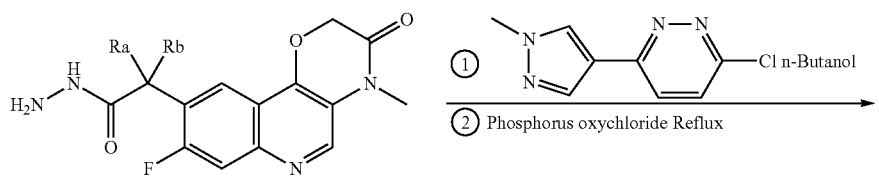

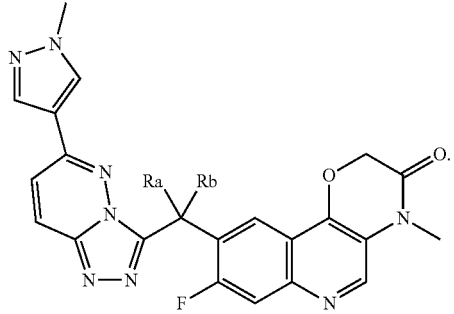

In the present invention, method 2 preferably comprises:

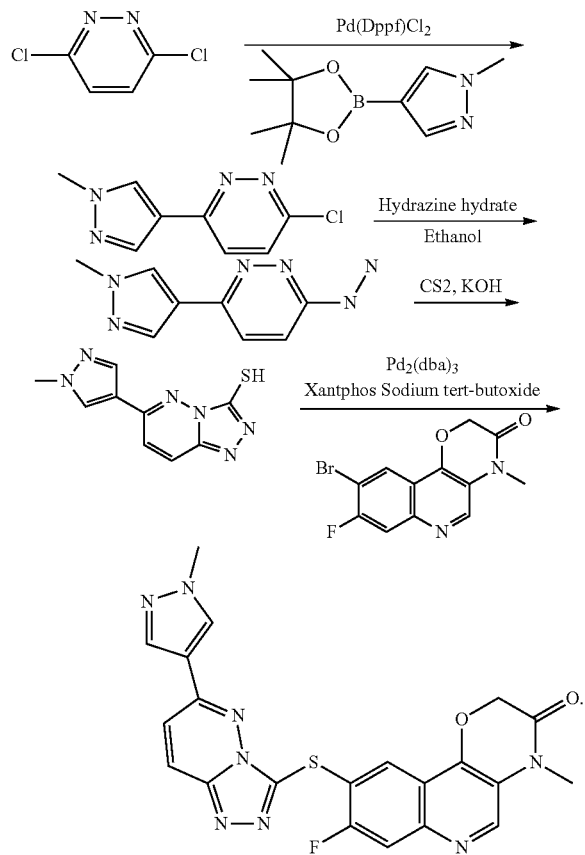

The present invention also provides a pharmaceutical composition, comprising: 1) a therapeutically effective dose of the quinoline derivative, a tautomer, a mesomer, a racemate, an enantiomer, a diastereomer, or a pharmaceutically acceptable salt thereof, and 2) a pharmaceutically acceptable carrier and/or excipient.

In the present invention, according to therapeutic purposes, the pharmaceutical composition can be formulated into various dosing unit dosage forms such as tablets, pills, powders, liquids, suspensions, emulsion, granules, capsules, suppositories and injections (solutions and suspensions) etc., preferably liquids, suspensions, emulsion, suppositories and injections (solutions and suspensions) etc.

In order to shape the pharmaceutical composition of tablets, any known and widely used excipients in the art can be used. For example, carriers, such as lactose, white sugar, sodium chloride, glucose, urea, starch, calcium carbonate, kaolin, crystalline cellulose and silicic acid etc.; adhesives, such as water, ethanol, propanol, ordinary syrup, glucose solution, starch solution, gelatin solution, carboxymethyl cellulose, shellac, methylcellulose and potassium phosphate, polyvinylpyrrolidone etc.; disintegrants, such as dry starch, sodium alginate, agar powder and kelp powder, sodium bicarbonate, calcium carbonate, fatty acid ester of polythene dehydrated sorbitol, sodium lauryl sulfate, stearic acid monoglyceride, starch and lactose etc.; disintegration inhibitors, such as white sugar, glyceryl tristearate, coconut oil and hydrogenated oil; adsorption accelerators, such as quaternary ammonium bases and sodium lauryl sulfate etc.; wetting agents, such as glycerin, starch etc.; adsorbents, such as starch, lactose, kaolin, bentonite and colloidal silicic acid etc.; and lubricants, such as pure talc, stearates, boric acid powder and polyethylene glycol, etc. It can also be made into sugar film-coated tablets, gelatin film-coated tablets, enteric film-coated tablets, film-coated tablets, double-layered film-coated tablets, and multilayer film-coated tablets by use of common coated materials when necessary.

In order to shape the pharmaceutical composition of pills, any known and widely used carriers and/or excipients in the art can be used. For example, carriers, such as lactose, starch, coconut oil, hardened vegetable oil, kaolin and talc etc.; adhesives, such as gum arabic powder, tragacanth powder, gelatin and ethanol etc.; disintegrants, such as agar and kelp powder etc.

In order to shape the pharmaceutical composition of suppositories, any known and widely used excipients in the art can be used. For example, polyethylene glycol, coconut oil, higher alcohols, higher alcohol esters, gelatin and semi-synthetic glycerides etc.

In order to produce the pharmaceutical composition of injections, the solution or suspension can be made into a blood-isotonic injection after being sterilized (preferably followed by adding an appropriate amount of sodium chloride, glucose, or glycerol and so on). In the preparation of injections, any commonly used carriers in the art can also be used. For example, water, ethanol, propylene glycol, ethoxylated isostearyl alcohol, polyoxylated isostearyl alcohol, fatty acid ester of polythene dehydrated sorbitol and so on. In addition, conventional solubilizers, buffers, analgesics and so on can also be added.

In the present invention, there is no special restriction on content of the quinoline derivative, the tautomer, the mesomer, the racemate, the enantiomer, the diastereomer, or the pharmaceutically acceptable salt thereof in the pharmaceutical composition. The content can be selected within a wide range, and usually accounts for 10 to 90 w/w % of the pharmaceutical composition, preferably 30 to 80 w/w %.

In the present invention, there is no special restriction on administration method of the composition. According to patients' age, sex, other conditions and symptoms, preparations of various dosage forms can be selected for administration. For example, tablets, pills, solutions, suspensions, emulsions, granules, or capsules can be administered orally; or, injections can be administered alone or in combination with infusion fluid for injection (such as glucose solution and amino acid solution) for intravenous injection; suppositories are administered to the rectum.

The present invention also provides a use of the quinoline derivative, the tautomer, the mesomer, the racemate, the enantiomer, the diastereomer, or the pharmaceutically acceptable salt thereof, or the pharmaceutical composition in preparing a medicament for regulating the catalytic activity of protein kinase, wherein the protein kinase is selected from c-Met receptor tyrosine kinases.

The present invention also provides a use of the quinoline derivative, the tautomer, the mesomer, the racemate, the enantiomer, the diastereomer, or the pharmaceutically acceptable salt thereof, or the pharmaceutical composition in preparing a medicament for treatment, alleviation and/or prevention of diseases associated with protein kinase, wherein said protein kinase is selected from c-Met receptor tyrosine kinases.

The diseases associated with protein kinase generally refer to cancer-related diseases, including cancer and cancer metastasis. The cancer can be bladder cancer, breast cancer, colon cancer, kidney cancer, liver cancer, lung cancer (non-small cell lung cancer), skin cancer, hematopoietic tumor of lymph system (including leukemia, acute lymphocytic leukemia, acute lymphoblastic lenkemia and so on), hematopoietic neoplasm of the bone marrow system (including acute and chronic myeloid leukemia, myelodysplastic syndrome, and promyelocytic leukemia), mesenchymal tumor (including fibrosarcoma and rhabdomyosarcoma and other sarcoma such as soft tissue sarcoma and osteosarcoma), tumor of central and peripheral nervous system (including astrocytoma, neuroblastoma, glioma, and nerve terminal tumor), and other tumors (including malignant melanoma, seminoma, teratocarcinoma, thyroid follicular and kaposi's sarcoma, etc.), preferably liver cancer, lung cancer, breast cancer, epidermal squamous carcinoma, or gastric cancer.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that: the quinoline derivatives of the present invention have c-Met inhibitory activity and can be used for treatment, alleviation and/or prevention of cancers or similar diseases. Thus it can provide a new direction for the development of c-Met inhibitors.

DETAILED DESCRIPTION OF THE PREFERRED EMBODIMENT

The following embodiments further illustrate the present invention, but the present invention is not limited thereto. The experimental methods that do not specify the specific conditions in the following embodiments are selected according to conventional methods and conditions, or according to the description of the product.

In the present invention, room temperature refers to 10 to 30° C.

Embodiment 1: Synthesis of 9-{difluoro(6-(1-methyl-1H-pyrazol-4-yl)-[1,2,4]triazolo[4,3-b]pyridazin-3-yl)methyl}-8-fluoro-4-methyl-2H-[1,4]oxazino[3,2-c]quinolin-3(4H)-one The synthetic route is as follows:

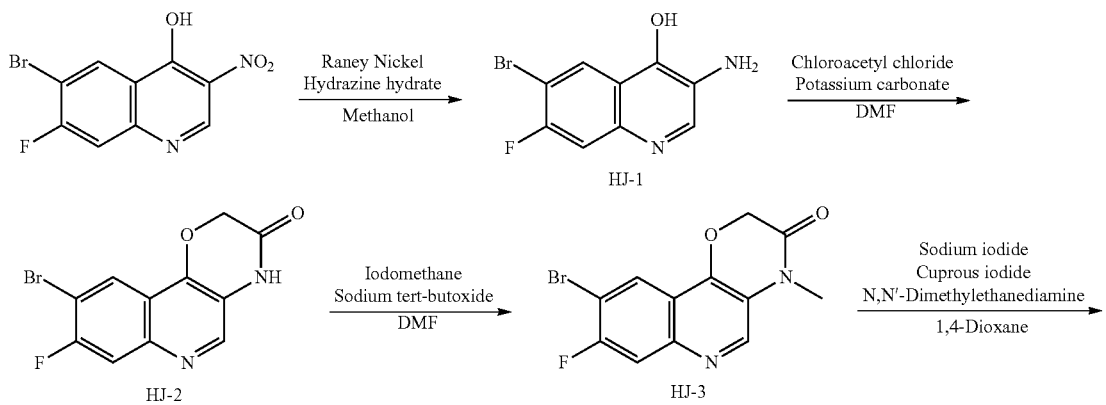

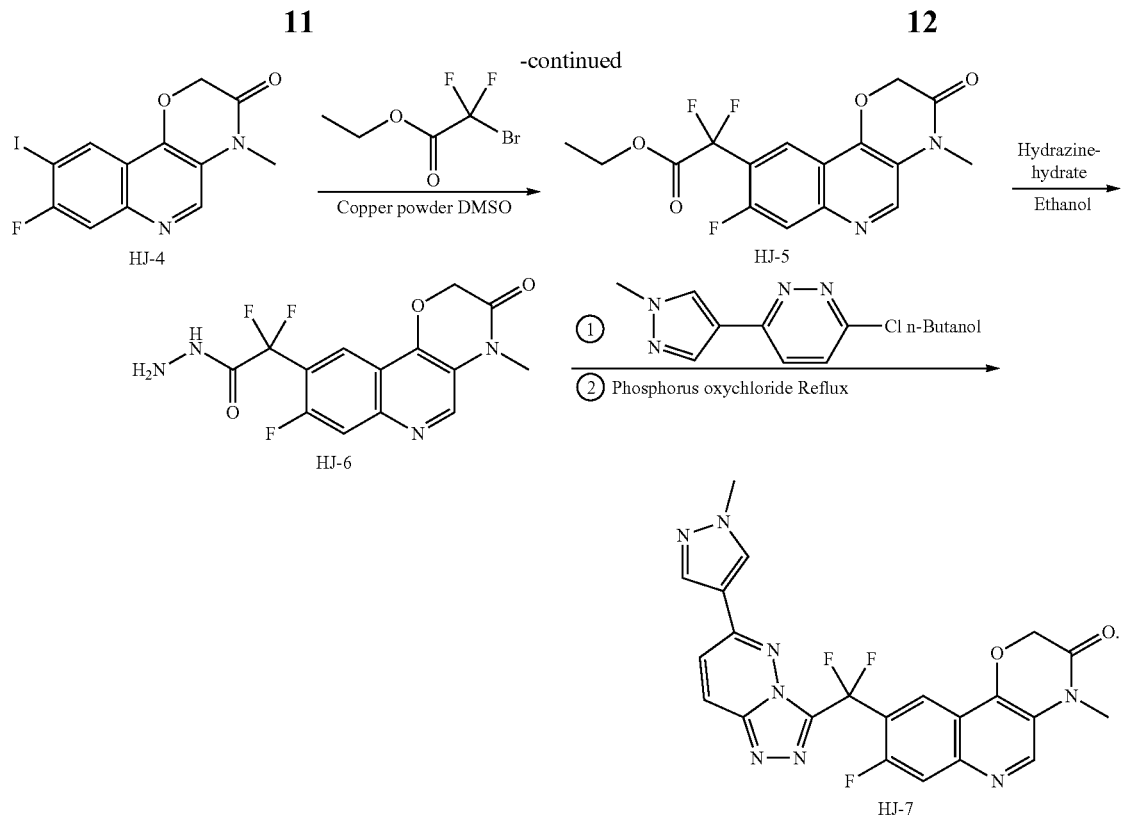

Step 1: Preparation of 3-amino-6-bromo-7-fluoro-quinolin-4-ol (HJ-1)

A compound 6-bromo-7-fluoro-3-nitroquinolin-4-ol (2.5 g, 9.0 mmol) and methanol (15 mL) were added to a 100 mL single-neck flask, then hydrazine hydrate (2.7 g, 46.5 mmol) and Raney Nickel (0.45 mmol) were added under an ice bath. The mixture was stirred at room temperature until the reaction was complete. Then the reaction solution was filtered, the filter cake was washed with methanol for three times, and the organic phase was rotary evaporated to give 2.20 g 3-amino-6-bromo-7-fluoro-quinolin-4-ol (HJ-1), yield 95%; MS m/z (ESI): 258.89 ([M+1]$^+$).

Step 2: Preparation of 9-bromo-8-fluoro-2H-[1,4]oxazino[3,2-c]quinolin-3(4H)-one (HJ-2)

(HJ-1) (2.10 g, 8.8 mmol) prepared in Step 1, potassium carbonate (3.64 g, 26.4 mmol) and anhydrous DMF (10 mL) were added to a 50 mL single-neck flask. The mixture was stirred at room temperature for 5 minutes, then chloroacetyl chloride (1.20 g, 10.6 mmol) was slowly dropwise added. TLC monitored the complete conversion of raw materials. The reaction solution was rotary evaporated, and the residual solid was separated by column chromatography to give 1.72 g 9-bromo-8-fluoro-2H-[1,4]oxazino[3,2-c]quinolin-3(4H)-one (HJ-2) as a light purple solid, yield 70%; MS m/z (ESI): 298.96 ([M+1]$^+$).

Step 3: Preparation of 9-bromo-8-fluoro-4-methyl-2H-[1,4]oxazino[3,2-c]quinolin-3(4H)-one (HJ-3)

(HJ-2) (1.35 g, 4.6 mmol) prepared in Step 2, sodium tert-butoxide (675 mg, 6.0 mmol), anhydrous DMF (10 mL) were added to a 50 mL single-neck flask, and the mixture was stirred at room temperature for 10 minutes, then methyl iodide (726 mg, 6.0 mmol) was added. The reaction was stopped after the complete conversion of the raw materials monitored by TLC. The reaction solution was rotary evaporated under reduced pressure, and the residual solid was separated by column chromatography to give 1.03 g 9-bromo-8-fluoro-4-methyl-2H-[1,4]oxazino[3,2-c]quinolin-3(4H)-one (HJ-3) as a pale yellow solid, yield 73%; MS m/z (ESI): 312.97 ([M+1]$^+$).

Step 4: Preparation of 8-fluoro-9-iodo-4-methyl-2H-[1,4]oxazino[3,2-c]quinolin-3(4H)-one (HJ-4)

(HJ-3) (1.03 g, 3.5 mmol) prepared in Step 3, sodium iodide (1.58 g, 10.5 mmol), cuprous iodide (133 mg, 0.7 mmol), N,N'-dimethylethylenediamine (138 mg, 1.58 mmol) and dioxane (8 mL) were successively added to a 25 mL sealed tube. The reaction solution was heated to 110° C. under nitrogen atmosphere. After reacting for 18 hours, the reaction solution was poured into ice water. The mixture was extracted with ethyl acetate and the organic phase was dried over anhydrous sodium sulfate, filtered, concentrated and separated by column chromatography to give 0.84 g 8-fluoro-9-iodo-4-methyl-2H-[1,4]oxazino[3,2-c]quinolin-3(4H)-one (HJ-4) as a pale yellow solid, yield 67%; MS m/z (ESI): 359.09 ([M+1]$^+$).

Step 5: Preparation of Ethyl 2,2-difluoro-2-(8-fluoro-4-methyl-3-oxo-3,4-dihydro-2H-[1,4]oxazino[3,2-c]quinolin-9-yl)acetate (HJ-5)

(HJ-4) (500 mg, 1.4 mmol) prepared in Step 4, nanoscale copper powder (198 mg, 3.1 mmol), ethyl bromodifluoroacetate (151 mg, 1.54 mmol) and DMSO (10 mL) were successively added to a 25 mL single-neck flask. The reaction solution was heated to 55° C. under nitrogen atmosphere and reacted for 18 hours. After the reaction was complete, the reaction solution was cooled to room temperature and poured into saturated ammonium chloride solution. The mixture was extracted with ethyl acetate, and the organic phase was dried over anhydrous sodium sulfate, filtered, concentrated and separated by column chromatography to give 258 mg ethyl difluoro(8-fluoro-4-methyl-3-oxo-3,4-dihydro-2H-[1,4]oxazino[3,2-c]quinolin-9-yl)acetate (HJ-5) as a white solid, yield 52%; MS m/z (ESI): 355.14 ([M+1]$^+$)

Step 6: Preparation of 2,2-difluoro-2-(8-fluoro-4-methyl-3-oxo-3,4-dihydro-2H-[1,4]oxazino[3,2-c]quinolin-9-yl)acetohydrazide (HJ-6)

(HJ-5) (200 mg, 0.56 mmol) prepared in Step 5, anhydrous methanol (10 mL) and hydrazine hydrate (0.3 mL) were successively added to a 25 mL single-neck flask. The reaction solution was heated to 55° C. and reacted for 30 minutes. After the reaction was complete, the reaction solution was concentrated and purified by column chromatography to give 130 mg 2,2-difluoro-2-(8-fluoro-4-methyl-3-oxo-3,4-dihydro-2H-[1,4]oxazino[3,2-c]quinolin-9-yl)acetohydrazide (HJ-6) as a pale yellow solid, yield 68%; MS m/z (ESI): 341.14 ([M+1]$^+$).

Step 7: Preparation of 9-{difluoro(6-(1-methyl-1H-pyrazol-4-yl)-[1,2,4]triazolo[4,3-b]pyridazin-3-yl) methyl}-8-fluoro-4-methyl-2H-[1,4]oxazino[3,2-c] quinolin-3(4H)-one (HJ-7)

(HJ-6) (100 mg, 0.29 mmol) prepared in Step 6, n-butanol (10 mL) and 3-chloro-6-(1-methyl-1H-pyrazol-4-yl) pyridazine (58 mg, 0.29 mmol) were successively added to a 25 mL single-neck flask. The reaction solution was heated to 130° C. and reacted for 2 hours. After the reaction was complete, the reaction solution was evaporated under reduced pressure to remove n-butanol. Then, acetonitrile (10 mL) and phosphorus oxychloride (45 mg, 0.29 mmol) were added to the reaction flask and the reaction solution was heated to reflux and reacted for 3 hours. After the reaction was complete, the reaction solution was poured into ice water and extracted with ethyl acetate. The organic phase was dried over anhydrous sodium sulfate, filtered, concentrated and purified by column chromatography to give 65 mg 9-{difluoro(6-(1-methyl-1H-pyrazol-4-yl)-[1,2,4]triazolo[4,3-b]pyridazin-3-yl)methyl}-8-fluoro-4-methyl-2H-[1,4]oxazino[3,2-c]quinolin-3(4H)-one (HJ-7) as a pale yellow solid, yield 47%; MS m/z (ESI): 481.23 ([M+1]$^+$).
$^1$H NMR (400 MHz, DMSO) δ 8.99 (s, 1H), 8.57-8.48 (m, 2H), 8.45 (s, 1H), 8.02 (d, J=3.5 Hz, 1H), 7.95 (d, J=12.1 Hz, 1H), 7.88 (d, J=9.8 Hz, 1H), 5.11 (s, 2H), 3.92 (s, 3H), 3.48 (s, 3H).

Embodiment 2: Synthesis of 8-fluoro-4-methyl-9-{[6-(1-methyl-1H-pyrazol-4-yl)-[1,2,4]triazolo[4,3-b] pyridazin-3-yl]sulfanyl}-2H-[1,4]oxazino[3,2-c] quinolin-3 (4H)-one The synthetic route is as follows:

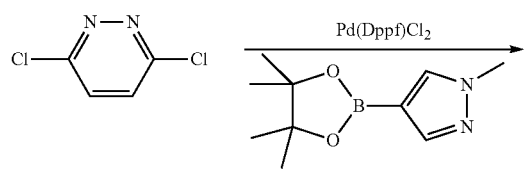

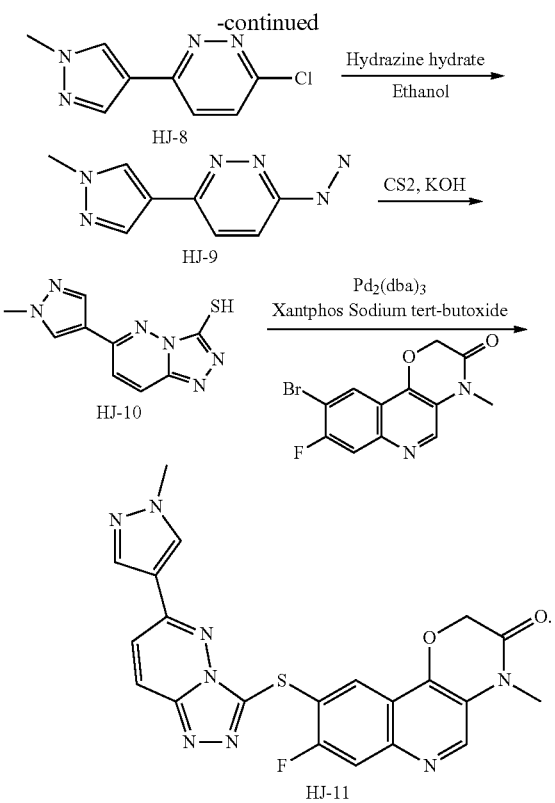

Step 1: Preparation of 3-chloro-6-(1-methyl-1H-pyrazol-4-yl)pyridazine (HJ-8)

Dioxane (67 mL) and water (27 mL) were added to a 250 mL three-neck flask as solvents, followed by successive addition of 3,6-dichloropyridazine (2.68 g, 18 mmol), potassium carbonate (6.0 g, 43.5 mmol), 1-methylpyrazole-4-boronic acid pinacol ester (2.99 g, 14.4 mmol), [1,1'-bis (diphenylphosphino)ferrocene]dichloropalladium (0.7 g, 0.96 mmol). The reaction solution was purged with nitrogen and heated to 80° C. After reacting for 10 hours, the reaction solution was concentrated and separated by column chromatography to give 1.96 g 3-chloro-6-(1-methyl-1H-pyrazol-4-yl)pyridazine (HJ-8) as a pale yellow solid, yield 70%; MS m/z (ESI): 195.12 ([M+1]$^+$).

Step 2: Preparation of 3-hydrazinyl-6-(1-methyl-1H-pyrazol-4-yl)pyridazine (HJ-9)

Ethanol (40 mL) was added to a 100 mL single-neck flask as a solvent, then (HJ-8) (1.90 g) prepared in Step 1 and hydrazine hydrate (3.5 mL) were successively added under an ice bath, and the ice bath was removed after the mixture was stirred for 10 minutes, then the mixture was heated to reflux. After reacting for 18 hours, the reaction solution was cooled to 10° C. and a white solid was precipitated out. The mixture was filtered with a Buchner funnel, and the filter cake was washed twice with cold ethanol and dried under vacuum to give 1.68 g 3-hydrazinyl-6-(1-methyl-1H-pyrazol-4-yl)pyridazine (HJ-9), yield 90%; MS m/z (ESI): 191.12 ([M+1]$^+$).

Step 3: Preparation of 6-(1-methyl-1H-pyrazol-4-yl)-[1,2,4]triazolo[4,3-b]pyridazine-3-thiol (HJ-10)

Ethanol (25 mL) was added to a 100 mL single-neck flask as a solvent, followed by successive addition of (HJ-9) (1.59 g, 8.4 mmol) prepared in Step 2 and a solution of potassium hydroxide (0.52 g, 9.2 mmol) in water (4 mL), then carbon disulfide (1.1 mL, 17.9 mmol) was added. After being purged with nitrogen, the reaction solution was heated to 70° C. After reacting for 4 hours, the reaction solution was rotary evaporated, and the residue was dissolved with 1N sodium hydroxide solution, then the insoluble substances were removed. The solution was adjusted to pH 2-3 with 1N hydrochloric acid and a solid precipitated out. The solid was filtered with suction, washed with water and dried under vacuum to give 1.50 g 6-(1-methyl-1H-pyrazol-4-yl)-[1,2,4]triazolo[4,3-b]pyridazine-3-thiol (HJ-10), yield 77%; MS m/z (ESI): 233.03 ([M+1]$^+$).

Step 4: Preparation of 8-fluoro-4-methyl-9-{[6-(1-methyl-1H-pyrazol-4-yl)-[1,2,4]triazolo[4,3-b]pyridazin-3-yl)sulfanyl}-2H-[1,4]oxazino[3,2-c]quinolin-3 (4H)-one (HJ-11)

(HJ-10) (44 mg, 0.188 mmol) prepared in Step 3, (HJ-2) (47 mg, 0.157 mmol) prepared in Step 2 of Embodiment 1, Pd$_2$(dba)$_3$ (10 mg, 0.016 mmol), Xantphos (20 mg, 0.032 mmol), sodium tert-butoxide (20 mg, 0.188 mmol) and anhydrous DMF (10 mL) were added to a 25 mL single-neck flask, then the mixture was heated to 100° C. under nitrogen atmosphere. After reacting for 24 hours, the reaction was stopped, and the reaction solution was rotary evaporated, the residual solid was separated by column chromatography to give 18 mg 8-fluoro-4-methyl-9-{[6-(1-methyl-1H-pyrazol-4-yl)-[1,2,4]triazolo[4,3-b]pyridazin-3-yl)sulfanyl}-2H-[1,4]oxazino[3,2-c]quinolin-3(4H)-one (HJ-11) as a pale yellow solid, yield 25%; MS m/z (ESI): 463.04 ([M+1]$^+$).

$^1$H NMR (400 MHz, DMSO) δ 8.85 (s, 1H), 8.51-8.39 (m, 2H), 8.20 (d, J=7.9 Hz, 1H), 8.07 (s, 1H), 7.88 (d, J=10.7 Hz, 2H), 7.78 (d, J=9.7 Hz, 1H), 4.97 (s, 2H), 3.92 (s, 3H), 3.41 (s, 3H).

Effect Embodiment 1: c-Met Kinase Activity Assay

The inhibitory ability of the compounds of the present invention on c-Met kinase activity was determined by Homogeneous Time-Resolved Fluorescence (HTRF), and was expressed by the median inhibitory concentration IC$_{50}$ value of the compounds. The method was as follows: a series of compounds with gradient concentration were incubated with a specific concentration of the enzyme solution for 5 minutes at room temperature, after which an appropriate amount of enzyme reaction substrate and ATP were added to start the enzyme reaction process. After 30 minutes, an appropriate amount of stop solution and detection solution were added, and the mixture was incubated for 1 hour. Then, the enzyme activity at specific compound concentrations was measured at wavelengths of 665 nm and 620 nm on Envision 2104 Multilabel Microcell Detector of PerkinElmer Company, and the inhibitory activity of the compound at different concentrations on enzyme activity was calculated, then the result was fitted to calculate the IC$_{50}$ value. The c-Met kinase used in this embodiment was purchased from Carna Biosciences, the test kit HTRF KinEASE-TK was purchased from Cisbio Bioassays Company, and ATP was purchased from Sigma Aldrich Company.

The activity of the compounds prepared in Embodiment 1 and Embodiment 2 of the present invention was determined by the above test, the obtained IC$_{50}$ values are shown in Table 1.

The positive control JNJ-38877605 was

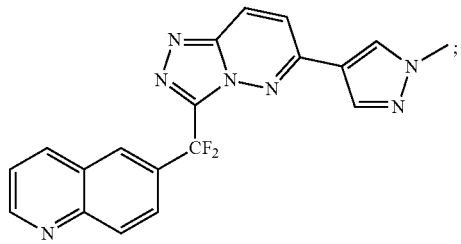 [SMILES: Cn1cc(-c2ccc3nnc(C(F)(F)c4ccc5ncccc5c4)n3n2)cn1]

referring to WO2007075567 (Embodiment 61).

TABLE 1

| Inhibitory activity of the compounds of the present invention on c-Met kinase | |
|---|---|
| Embodiment number | IC$_{50}$ (c-Met/BIO) (nM) |
| 1 | 1.0 |
| 2 | 2.2 |
| positive control JNJ-38877605 | 4.9 |

Conclusion: Both the compounds of the present invention have a significant inhibitory effect on c-Met kinase activity.

Effect Embodiment 2: c-Met Cell Proliferation Inhibition Test

The inhibitory activity of the test compound on proliferation of human gastric cancer cells SNU-5 with high expression of c-Met was determined through the following in vitro cell assay, and the activity can be expressed by IC$_{50}$ value. Specific experimental method can refer to Neru Munshi, Sebastien Jeay, Youzhi Li, et al., *ARQ 197, a Novel and Selective Inhibitor of the Human c-Met Receptor Tyrosine Kinase with Antitumor Activity. Mol Cancer Ther* 2010; 9:1544-1553, the content of which is incorporated herein by reference in its entirety. The general method is as follows: first, human tumor cells SNU-5 (purchased from the Institute of Biochemistry and Cell Biology) with high expression of c-Met was selected and inoculated on a 96-well culture plate at a suitable cell concentration (e.g., 5000 cells/ml culture medium), then they were diluted with IMDM culture medium containing 2% FBS to form a series of test compound solutions at gradient concentrations (generally 6 to 7 concentrations) and continuously incubated for 72 hours. After 72 hours, the activity of the test compound on inhibiting cell proliferation could be determined using the Cell Counting Kit-8 (CCK-8, purchased from DojinDo) method. The IC$_{50}$ value can be calculated from the inhibitory values on cell proliferation of the test compound at a series of different concentrations.

The activity of the compounds prepared in Embodiment 1 and Embodiment 2 of the present invention was determined by the above test, the obtained IC$_{50}$ values are shown in Table 2.

TABLE 2

Inhibitory activity of the embodiment compounds of the present invention on proliferation of SNU-5 cells

| Embodiment number | $IC_{50}$ (SNU-5) (nM) |
|---|---|
| 1 | 1.2 |
| 2 | 2.8 |
| positive control JNJ-38877605 | 4.7 |

Conclusion: All the compounds of the present invention have significant inhibitory activity on proliferation of SNU-5 cells.

What is claimed is:

1. A quinoline derivative, a tautomer, a mesomer, a racemate, an enantiomer, a diastereomer, or a pharmaceutically acceptable salt thereof, wherein the quinoline derivative is of the formula:

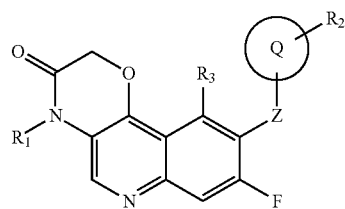

wherein,
$R_1$ is a $C_{1-3}$ alkyl;
$R_2$ is

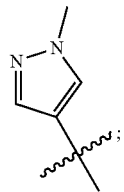

$R_3$ is a hydrogen;
Z is —$CR^aR^b$ or S; $R^a$ and $R^b$ are each independently a hydrogen, a $C_{1-3}$ alkyl, or a halogen;
Q ring is

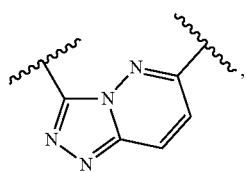 [SMILES: *c1ccc2nnc(*)n2n1]

wherein the triazole moiety links to Z.

2. The quinoline derivative, the tautomer, the mesomer, the racemate, the enantiomer, the diastereomer, or the pharmaceutically acceptable salt thereof according to claim 1, wherein,
in the definition of $R_1$, $R^a$, and $R^b$, the $C_{1-3}$ alkyl is independently selected from methyl, ethyl, or isopropyl;
and/or, in the definition of $R^a$ and $R^b$, the halogen is independently fluorine, chlorine, bromine, or iodine.

3. The quinoline derivative, the tautomer, the mesomer, the racemate, the enantiomer, the diastereomer, or the pharmaceutically acceptable salt thereof according to claim 1, wherein the quinoline derivative is selected from the compound consisting of

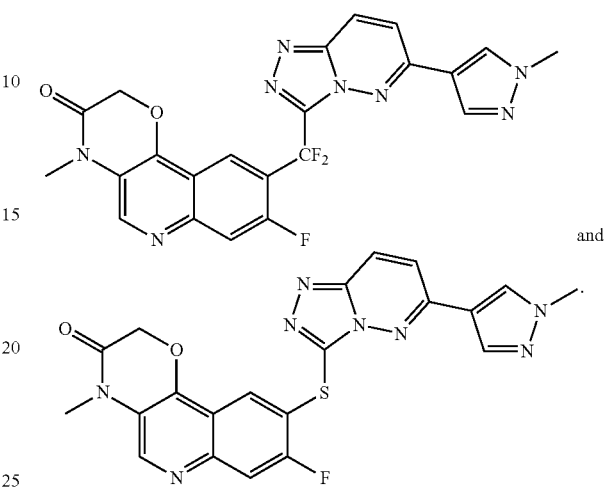

and

4. A preparation method for the quinoline derivative, the tautomer, the mesomer, the racemate, the enantiomer, the diastereomer, or the pharmaceutically acceptable salt thereof according to claim 1, which is selected from
method 1, when Z is —$CR^aR^b$, the method comprises:

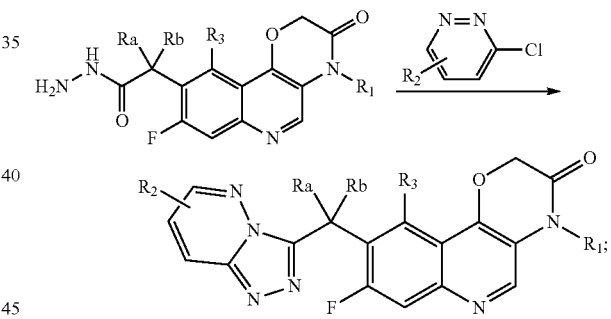

method 2, when Z is S, the method comprises:

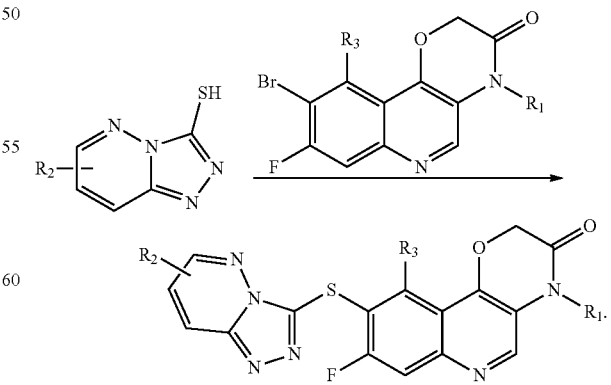

5. A pharmaceutical composition, comprising 1) a therapeutically effective dose of the quinoline derivative, the tautomer, the mesomer, the racemate, the enantiomer, the diastereomer, or the pharmaceutically acceptable salt thereof according to claim 1, and 2) a pharmaceutically acceptable carrier and/or excipient.

6. A method for regulating the catalytic activity of protein kinase in a subject in need thereof, comprising: administering an effective amount of the quinoline derivative, the tautomer, the mesomer, the racemate, the enantiomer, the diastereomer, or the pharmaceutically acceptable salt thereof according to claim 1 to the subject, wherein the protein kinase is selected from c-Met receptor tyrosine kinases.

7. A method for treating, and/or alleviating cancer in a subject in need thereof, comprising: administering an effective amount of the quinoline derivative, the tautomer, the mesomer, the racemate, the enantiomer, the diastereomer, or the pharmaceutically acceptable salt thereof according to claim 1 to the subject.

8. A method for regulating the catalytic activity of protein kinase in a subject in need thereof, comprising: administering an effective amount of the pharmaceutical composition according to claim 5 to the subject, wherein the protein kinase is selected from c-Met receptor tyrosine kinases.

9. A method for treating, and/or alleviating cancer in a subject in need thereof, comprising: administering an effective amount of the pharmaceutical composition according to claim 5 to the subject.

10. The method according to claim 7, wherein the cancer is selected from the group consisting of bladder cancer, breast cancer, colon cancer, kidney cancer, liver cancer, lung cancer, skin cancer, epidermal squamous cell carcinoma, gastric cancer, hematopoietic tumor of lymph system, hematopoietic tumor of bone marrow system, mesenchymal tumor, and tumor of central and peripheral nervous system.

11. The method according to claim 9, wherein the cancer is selected from the group consisting of bladder cancer, breast cancer, colon cancer, kidney cancer, liver cancer, lung cancer, skin cancer, epidermal squamous cell carcinoma, gastric cancer, hematopoietic tumor of lymph system, hematopoietic tumor of bone marrow system, mesenchymal tumor, and tumor of central and peripheral nervous system.

\* \* \* \* \*